United States Patent [19]
Guillet et al.

[11] Patent Number: 5,672,790
[45] Date of Patent: Sep. 30, 1997

[54] PROCESS FOR THE HYDROGENOLYSIS OF CHLOROFLUOROCARBONS AND OF CHLOROFLUOROHYDROCARBONS

[75] Inventors: Dominique Guillet, Vernaison; Serge Hub, Lyons, both of France

[73] Assignee: Elf Atochem S.A., France

[21] Appl. No.: 616,564

[22] Filed: Mar. 15, 1996

[30] Foreign Application Priority Data

Mar. 17, 1995 [FR] France .................. 95 03117

[51] Int. Cl.$^6$ .................. C07C 17/10; C07K 19/08
[52] U.S. Cl. .................. 570/176
[58] Field of Search .................. 570/176

[56] References Cited

U.S. PATENT DOCUMENTS

| 5,136,113 | 8/1992 | Rao | 570/176 |
| 5,191,118 | 3/1993 | Correia et al. | 562/604 |
| 5,278,122 | 1/1994 | Correia et al. | 502/185 |
| 5,481,051 | 1/1996 | Rao | 570/176 |

FOREIGN PATENT DOCUMENTS

| A-0506515 | 9/1992 | European Pat. Off. . |
| A-2 645 531 | 10/1990 | France . |
| WO-A-9402439 | 2/1994 | WIPO . |

*Primary Examiner*—Joseph McKane
*Assistant Examiner*—Richard S. Myers, Jr.

[57] ABSTRACT

The invention relates to the gas-phase hydrogenolysis of chlorofluorocarbons or of chlorofluorohydrocarbons in the presence of a palladium-based catalyst deposited on a support in which sulfur is incorporated into the catalyst in order to stabilize the catalytic activity.

12 Claims, No Drawings

PROCESS FOR THE HYDROGENOLYSIS OF CHLOROFLUOROCARBONS AND OF CHLOROFLUOROHYDROCARBONS

FIELD OF THE INVENTION

The present invention relates to a process for the hydrogenolysis of chlorofluorocarbons (CFCs) and of chlorofluorohydrocarbons (CFHCs).

BACKGROUND OF THE INVENTION

It appears nowadays to be clearly established that the factors responsible for the decrease of the ozone layer in the stratosphere are chlorofluorocarbons. The reason for this is that liberated CFCs tend to percolate slowly up to the stratosphere, where they decompose by photodissociation releasing monoatomic chlorine. The chlorine atom destroys the $O_3$ (ozone) molecules in the course of catalytic cycles in which it is regenerated, thereby being able to affect several molecules. The international community has thus decided to abandon the production of CFC and it has consequently become necessary to find and produce acceptable substitutes.

CFCs are composed, as their name suggests, of chlorine, fluorine and carbon atoms, but lack hydrogen. One strategy envisaged by producers consists in replacing them by molecules containing the same elements plus hydrogen, which are thus less stable and are capable of degrading rapidly in the lower atmosphere. The ultimate aim will consist in using compounds lacking chlorine, fluorohydrocarbons (FHCs), which should have no impact on ozone.

In this context, hydrogenolysis which replaces a chlorine atom by a hydrogen atom in a molecule constitutes a reaction which is particularly well suited to the problem posed.

The potential of this reaction is demonstrated in numerous patents. Thus, the hydrogenolysis of chlorodifluoromethane to difluoromethane is described in patent EP 0,508,660, and those of chlorotetrafluoroethane and dichlorotetrafluoromethane to tetrafluoroethane are mentioned in patents GB 1,578,933, EP 0,349,115 and U.S. Pat. No. 4,873,381. This type of reaction also constitutes a good means of purifying the FHCs of the CFCs which may be present, as described in patent application WO 94/02439 for pentafluoroethane.

However, the main drawback of hydrogenolysis processes lies in the stability of the catalytic activity over time. Indeed, under the often severe reaction conditions necessary for the complete conversion of the reactants, the catalyst becomes deactivated over time. It is thus necessary to replace it periodically with a new charge or to find an effective means of regenerating the spent catalyst.

In this respect, several techniques for regenerating hydrogenolysis catalysts are described in the literature. Patent application WO 93/24224 proposes an oxidation of the spent catalyst with oxygen or an oxidizing agent. Treatments with chlorine (U.S. Pat. No. 5,057,470) or with the CFC which may be the reactant to convert (U.S. Pat. No. 4,980,324) also proved to be effective. However, these processes only reactivate the catalysts, which still have the same drawbacks after the treatment.

DESCRIPTION OF THE INVENTION

It has now been found that the incorporation of sulphur into a palladium-based catalyst deposited on a support imparts to this catalyst the property of being stable in gas-phase hydrogenolysis reactions, both in reactions for the synthesis of FHC from CFC or from CFHC, and in processes for the purifying of CFC impurities contained in the FHCs.

The sulphur treatment of a hydrogenation/hydrogenolysis catalyst is known from patent FR 2,645,531, which describes the treatment of a Pd/C catalyst with sulphur-containing compounds to increase the selectivity for the liquid-phase hydrogenolysis of dichloroacetic acid ($HCl_2C-COOH$) to monochloroacetic acid ($H_2ClC-COOH$). However, it was totally unexpected that treatment of the catalyst with a sulphur compound would allow its activity to be stabilized in the gas-phase hydrogenolysis of CFC or of CFHC, all the more so since the final research report from J. D. Part and J. R. Lacher published in 1959, which research was financed by the Air Force Office of Scientific Research (No. TR5899) and the Armed Services Technical Informations Agency (No. AD 162198), describes a treatment of the support to remove the sulphur before impregnation with palladium.

The subject of the invention is thus a process for the gas-phase hydrogenolysis of chlorofluorocarbons or of chlorofluorohydrocarbons in the presence of a palladium-based catalyst deposited on a support, characterized in that sulphur is incorporated into the catalyst.

In the catalyst according to the invention, the support may be charcoal, a fluoroalumina or aluminium fluoride, and the palladium is advantageously deposited onto this support at a proportion of from 0.1 to 10% by weight relative to the total weight of the catalyst (Pd+support).

The amount of sulphur to be incorporated into the catalyst may range from 0.75 to 750 mg of sulphur per gram of palladium. It is preferably between 2 and 100 mg of sulphur per gram of palladium and more particularly between 7.5 and 75 mg of sulphur per gram of palladium.

The sulphur may be incorporated into the catalyst before and/or during its use. The incorporation may be performed in various ways depending on whether the sulphur-containing precursor compound is normally liquid (for example $SCl_2$, $S_2Cl_2$, $CS_2$, thiophene, dimethyl sulphide, etc.) or gaseous (for example $H_2S$, methyl mercaptan, etc.).

When the sulphur-containing precursor compound is a liquid, the process may be performed by impregnation in the presence of a solvent whose choice depends on the nature of the sulphur-containing precursor. In the case of $CS_2$, ethanol is particularly suitable; however, any solvent for $CS_2$ may be used. After the impregnation, the catalyst is heat-treated under an atmosphere of a gas which may be inert, although hydrogen is preferably used, at a temperature of between 150° and 400° C. to decompose the sulphur-containing compound.

When the sulphur-containing precursor is normally gaseous ($H_2S$, $H_3C-SH$) or is a liquid which has a high vapor pressure (for example, $CS_2$), it may be introduced onto the catalyst via the gaseous phase before or during admission of the hydrogen and the reactant to be hydrogenolyzed. In this particularly advantageous technique for the "in situ" treatment of the catalyst in the reaction, the amount of sulphur introduced onto the catalyst may be adjusted to the levels mentioned previously by varying the concentration of the sulphur-containing compound of the gas, the flow rate of the gas and the duration of the treatment.

Irrespective of the sulphur-containing compound and its mode of incorporation, the introduction of sulphur followed by a heat treatment leads to the formation of a solid phase of sulphur and palladium of formula $Pd_4S$. However, total conversion of the available palladium is not necessary to obtain a stable catalyst.

The operating conditions for the hydrogenolysis reaction may vary within a wide range depending on the nature of the reactant to be hydrogenolyzed (CFC or CFHC):

The reaction temperature is generally between 100° and 450° C., but it is preferred to work between 150° and 350° C.

The pressure may range from 1 to 50 bar; an increase in pressure has the effect of increasing the contact time and thus of making possible to achieve high conversions for a given temperature.

The hourly flow rate of reactant fed continuously into the reactor may range from 0.01 to 12 mol per liter of catalyst.

The $H_2$/reactant molar ratio is generally between 0.5 and 10, preferably between 1 and 6.

As non-limiting examples of reactants to which the process according to the invention applies, mention may be made more particularly of chloropentafluoroethane (F115), 1,1-dichloro-1,2,2,2-tetrafluoroethane (F114a), chlorodifluormethane (F22), 1-chloro-1,1-difluoroethane (F142b) and 1-chloro-1,2,2,2-tetrafluoroethane (F124), the hydrogenolysis of which leads respectively to pentafluoroethane (F125), 1,1,1,2-tetrafluoroethane (F134a), difluoromethane (F32), 1,1-difluoroethane (F152a) and 1,1,1,2-tetrafluoroethane (F134a). Mention may also be made of $C_3$ chlorofluoro(hydro)carbons such as 1,2,2-trichloro-1,1,3,3,3-pentafluoropropane (F215aa) or 1,2-dichloro-1,1,3,3,3-pentafluoropropane (F225da) the hydrogenolysis of which leads to 1,1,1,3,3-pentafluoropropane (F245fa).

EXAMPLES

The examples which follow illustrate the invention without limiting it. The percentages relating to the selectivities are expressed in moles.

EXAMPLE 1

Comparative 75 ml of a commercial Pd/C catalyst containing 3% by weight of palladium are introduced into a tubular Inconel reactor 45 cm in length and 2.72 cm in internal diameter. Prior to the introduction of the reactants, the catalyst is reduced at 300° C. under an atmospheric pressure of hydrogen.

A mixture of hydrogen, pentafluoroethane (F125) and chloropentafluoroethane (F115) are passed over the catalyst under the following operating conditions:

Temperature: 330° C.

Flow rate of hydrogen: 0.107 mol/hour

Flow rate of F125: 0.286 mol/hour

Flow rate of F115: 0.018 mol/hour

Analysis is performed by chromatography (GC) in line at the reactor outlet. The results collated in the following table show a rapid decrease in the activity of the catalyst over time.

| TIME | CONVERSION | SELECTIVITY (%) FOR | | |
|---|---|---|---|---|
| (hours) | (%) of F115 | F125 | F134a | F143a |
| 11 | 90.3 | 93.8 | 1.4 | 4.8 |
| 32 | 88.0 | 94.9 | 1.0 | 4.1 |
| 40 | 86.2 | 95.1 | 1.0 | 3.9 |
| 60 | 83.3 | 95.3 | 1.0 | 3.7 |
| 68 | 82.3 | 95.3 | 1.1 | 3.6 |
| 80 | 81.3 | 95.4 | 1.0 | 3.6 |
| 92 | 77.9 | 95.6 | 1.0 | 3.4 |
| 100 | 77.9 | 95.6 | 0.9 | 3.5 |
| 108 | 76.5 | 95.7 | 1.0 | 3.3 |
| 122 | 75.1 | 95.6 | 1.0 | 3.4 |
| 130 | 73.7 | 95.5 | 1.1 | 3.4 |
| 148 | 70.9 | 95.7 | 0.9 | 3.4 |
| 170 | 67.8 | 95.7 | 1.0 | 3.3 |
| 190 | 64.3 | 95.5 | 1.0 | 3.5 |
| 208 | 61.3 | 95.7 | 0.9 | 3.4 |
| 230 | 57.2 | 95.9 | 0.8 | 3.3 |
| 252 | 54.8 | 95.8 | 0.9 | 3.3 |
| 268 | 52.0 | 95.9 | 0.9 | 3.2 |
| 289 | 49.0 | 95.8 | 0.8 | 3.4 |
| 308 | 45.0 | 96.0 | 0.9 | 3.1 |

EXAMPLE 2 a) Treatment of the catalyst 75 ml of the same commercial Pd/C catalyst as in the above example are loaded into a rotary evaporator, followed by introduction of 100 ml of an ethanol solution containing 0.011 mol/liter of $CS_2$. The solid is maintained in contact with the solution at 20° C. for 20 hours. The catalyst is then recovered by filtration, followed by reduction at 300° C. under an atmospheric pressure of hydrogen for 4 hours. The amount of sulphur bound is 0.2% by weight and X-ray diffraction demonstrates the formation of a $Pd_4S$ phase.

b) Purification of the F125

75 ml of the catalyst prepared above are introduced into the same tubular reactor as in Example 1, followed by passage of a mixture of hydrogen, pentafluoroethane (F125) and chloropentafluoroethane (F115) over this catalyst under the following operating conditions:

Temperature: 330° C.

Flow rate of hydrogen: 0.107 mol/hour

Flow rate of F125: 0.286 mol/hour

Flow rate of F115: 0.018 mol/hour

The results of the analysis performed by chromatography (GC) in line at the reactor outlet are collated in the following table. Appreciable stability of the catalytic activity is observed.

| TIME | CONVERSION | SELECTIVITY (%) FOR | | |
|---|---|---|---|---|
| (hours) | (%) of F115 | F125 | F134a | F143a |
| 27 | 59.4 | 76.2 | 6.4 | 17.4 |
| 35 | 60.4 | 76.9 | 6.2 | 16.9 |
| 45 | 60.0 | 81.9 | 6.4 | 11.7 |
| 65 | 63.8 | 84.4 | 5.9 | 9.7 |
| 77 | 61.6 | 84.6 | 6.0 | 9.4 |
| 79 | 63.7 | 84.8 | 5.7 | 9.5 |
| 95 | 60.8 | 84.2 | 6.3 | 9.5 |
| 105 | 63.0 | 85.2 | 5.6 | 9.2 |
| 115 | 62.7 | 84.3 | 5.9 | 9.8 |
| 125 | 62.7 | 84.8 | 5.6 | 9.6 |
| 143 | 62.5 | 84.7 | 5.6 | 9.7 |
| 157 | 62.8 | 83.0 | 5.4 | 11.6 |
| 164 | 65.9 | 86.7 | 5.1 | 8.2 |
| 197 | 65.6 | 86.7 | 5.1 | 8.2 |
| 208 | 62.8 | 87.5 | 5.2 | 7.3 |
| 212 | 61.4 | 85.8 | 5.5 | 8.7 |
| 234 | 62.6 | 85.6 | 5.1 | 9.3 |

-continued

| TIME | CONVERSION | SELECTIVITY (%) FOR | | |
|---|---|---|---|---|
| (hours) | (%) of F115 | F125 | F134a | F143a |
| 254 | 62.0 | 85.9 | 5.1 | 9.0 |
| 265 | 62.7 | 86.7 | 5.2 | 8.1 |
| 292 | 63.1 | 87.6 | 5.1 | 7.3 |
| 296 | 63.5 | 87.5 | 4.9 | 7.6 |
| 313 | 63.5 | 88.5 | 5.0 | 6.5 |

EXAMPLE 3 a) Treatment of the catalyst

The process is performed as in Example 2a, but with 100 ml of an ethanol solution containing 0.001 mol/liter of $CS_2$. X-ray diffraction detects no $Pd_4S$ crystallized phase, but the sulphur analysis shows the presence of 500 ppm by weight of sulphur on the catalyst.

b) Purification of the F125

With the catalyst thus treated and the process being performed as in Example 2b, the results collated in the following table were obtained:

| TIME | CONVERSION | SELECTIVITY (%) FOR | | |
|---|---|---|---|---|
| (hours) | (%) of F115 | F125 | F134a | F143a |
| 21 | 65.8 | 86.7 | 4.9 | 8.4 |
| 46 | 62.6 | 87.6 | 4.6 | 7.8 |
| 70 | 62.7 | 88.5 | 4.6 | 6.9 |
| 80 | 62.8 | 88.7 | 4.4 | 6.9 |
| 96 | 61.0 | 88.2 | 4.5 | 7.3 |
| 101 | 61.6 | 89.2 | 4.3 | 6.5 |
| 115 | 58.9 | 88.6 | 4.5 | 6.9 |
| 127 | 59.9 | 88.8 | 4.0 | 7.2 |
| 176 | 61.2 | 89.4 | 3.8 | 6.8 |
| 185 | 62.6 | 90.6 | 3.5 | 5.9 |
| 195 | 61.9 | 90.2 | 3.4 | 6.4 |
| 205 | 62.0 | 90.8 | 3.5 | 5.7 |
| 215 | 61.0 | 90.2 | 3.5 | 6.3 |
| 243 | 61.6 | 91.1 | 3.1 | 5.8 |
| 251 | 61.6 | 90.7 | 3.1 | 6.2 |
| 273 | 58.4 | 90.5 | 3.3 | 6.2 |
| 315 | 58.7 | 90.7 | 3.1 | 6.2 |
| 325 | 61.0 | 91.0 | 3.0 | 6.0 |

The level of conversion is the same as in Example 2a with the same stability over time. An improvement in the selectivity for F125 is also noted.

EXAMPLE 4

Comparative 75 ml of a commercial Pd/C catalyst containing 2% by weight of palladium are introduced into a tubular Inconel reactor 45 cm in length and 2.72 cm in internal diameter. Prior to the introduction of the reactants, the catalyst is reduced at 300° C. under an atmospheric pressure of hydrogen.

A mixture of hydrogen, pentafluoroethane (F125) and chloropentafluoroethane (F115) are passed over the catalyst under the following operating conditions:

Temperature: 250° C.

Flow rate of hydrogen: 0.103 mol/hour

Flow rate of F125: 0.281 mol/hour

Flow rate of F115: 0.018 mol/hour

The analysis performed by chromatography (GC) in line at the reactor outlet gives the results collated in the following table. A decrease in the activity of the catalyst over time is noted.

| TIME | CONVERSION | SELECTIVITY (%) FOR | | |
|---|---|---|---|---|
| (hours) | (%) of F115 | F143a | F125 | F134a |
| 31 | 43.1 | 12.9 | 84.6 | 2.5 |
| 50 | 40.9 | 13.0 | 84.2 | 2.8 |
| 75 | 40.0 | 12.8 | 84.9 | 2.3 |
| 80 | 40.4 | 12.4 | 85.4 | 2.2 |
| 143 | 38.2 | 11.1 | 86.6 | 2.3 |
| 177 | 36.9 | 18.0 | 79.8 | 2.2 |
| 180 | 37.6 | 14.2 | 83.8 | 2.0 |
| 193 | 36.6 | 13.0 | 84.8 | 2.2 |
| 218 | 34.4 | 14.6 | 83.0 | 2.4 |
| 241 | 33.8 | 15.7 | 81.8 | 2.5 |
| 260 | 33.0 | 15.0 | 82.5 | 2.5 |
| 270 | 32.6 | 15.7 | 81.9 | 2.4 |
| 290 | 32.1 | 16.0 | 81.7 | 2.3 |
| 330 | 30.0 | 15.6 | 82.0 | 2.4 |
| 350 | 29.8 | 15.2 | 82.3 | 2.5 |
| 390 | 28.3 | 16.0 | 81.6 | 2.4 |
| 415 | 27.4 | 15.0 | 82.7 | 2.3 |
| 430 | 27.1 | 15.7 | 82.0 | 2.3 |
| 450 | 26.1 | 16.0 | 81.7 | 2.3 |
| 500 | 24.0 | 15.6 | 82.1 | 2.3 |

EXAMPLE 5

75 ml of the same commercial 2% Pd/C catalyst as in Example 4 are introduced into the same reactor as in Example 4. Prior to the introduction of the reactants, the catalyst is treated with hydrogen containing 100 ppm of hydrogen sulphide ($H_2S$) at room temperature for 60 hours with a gas flow rate of 6 l/h. The catalyst is then reduced at 300° C. under an atmospheric pressure of hydrogen. X-ray diffraction demonstrates the formation of a $Pd_4S$ phase.

A mixture of hydrogen, pentafluoroethane (F125) and chloropentafluoroethane (F115) are passed over the catalyst under the following operating conditions:

Temperature: 250° C.

Flow rate of hydrogen: 0.103 mol/hour

Flow rate of F125: 0.281 mol/hour

Flow rate of F115: 0.018 mol/hour

The analysis performed by chromatography (GC) in line at the reactor outlet gives the results collated in the following table. Constant activity of the catalyst over time is noted.

| TIME | CONVERSION | SELECTIVITY (%) FOR | | |
|---|---|---|---|---|
| (hours) | (%) of F115 | F143a | F125 | F134a |
| 10 | 32.4 | 35.2 | 64.8 | 1.0 |
| 21 | 31.8 | 36.8 | 62.2 | 1.0 |
| 30 | 32.8 | 34.9 | 63.7 | 1.4 |
| 40 | 32.5 | 35.1 | 63.8 | 1.1 |
| 72 | 32.0 | 32.6 | 65.9 | 1.5 |
| 140 | 31.3 | 33.3 | 65.5 | 1.2 |
| 150 | 32.3 | 27.3 | 71.3 | 1.4 |
| 165 | 32.0 | 27.5 | 71.2 | 1.3 |
| 189 | 32.0 | 26.5 | 72.0 | 1.5 |
| 250 | 32.1 | 24.8 | 73.7 | 1.5 |
| 280 | 32.6 | 22.0 | 76.5 | 1.5 |
| 290 | 31.8 | 21.5 | 77.0 | 1.5 |
| 306 | 33.0 | 21.1 | 77.4 | 1.5 |
| 350 | 32.3 | 19.5 | 79.0 | 1.5 |
| 395 | 31.8 | 19.0 | 79.5 | 1.5 |
| 430 | 32.4 | 18.1 | 80.4 | 1.5 |

| TIME | CONVERSION | SELECTIVITY (%) FOR | | |
|---|---|---|---|---|
| (hours) | (%) of F115 | F143a | F125 | F134a |
| 450 | 31.5 | 18.0 | 80.5 | 1.5 |
| 500 | 32.2 | 17.6 | 80.9 | 1.5 |

EXAMPLE 6 a) Treatment of the catalyst 75 ml of the same commercial 2% Pd/C catalyst as in Example 4 are loaded into a rotary evaporator, followed by introduction of 100 ml of an ethanol solution containing 0.007 mol/liter of $CS_2$. The solid is maintained in contact with the solution at 20° C. for 20 hours. The catalyst is then recovered by filtration, followed by reduction at 300° C. under an atmospheric pressure of hydrogen for 4 hours. The amount of sulphur bound is 0.15% by weight and X-ray diffraction demonstrates the formation of a $Pd_4S$ phase.

b) Synthesis of the F125

75 ml of the catalyst prepared above are introduced into the same tubular reactor as in Example 4, followed by passage of a mixture of hydrogen and chloropentafluoroethane (F115) into the reactor under the following operating conditions:

Temperature: 250° C.

Flow rate of hydrogen: 0.147 mol/hour

Flow rate of F115: 0.026 mol/hour

The results of the analyses performed by chromatography (GC) in line at the reactor outlet are collated in the following table. Good stability of the activity of the catalyst over time is noted.

| TIME | CONVERSION | SELECTIVITY (%) FOR | | |
|---|---|---|---|---|
| (hours) | (%) of F115 | F125 | F143a | F134a |
| 175 | 47.8 | 81.7 | 16.2 | 2.1 |
| 181 | 47.4 | 82.1 | 15.9 | 2.0 |
| 191 | 47.1 | 82.5 | 15.5 | 2.0 |
| 201 | 46.9 | 83.0 | 15.0 | 2.0 |
| 211 | 47.3 | 83.7 | 14.4 | 1.9 |
| 219 | 47.2 | 83.8 | 14.3 | 1.9 |
| 229 | 47.0 | 83.9 | 14.1 | 2.0 |
| 239 | 45.8 | 83.2 | 14.7 | 2.1 |
| 251 | 45.8 | 83.3 | 14.6 | 2.1 |
| 261 | 45.4 | 83.3 | 14.6 | 2.1 |
| 271 | 45.4 | 83.1 | 14.7 | 2.2 |
| 281 | 45.2 | 83.1 | 14.7 | 2.2 |
| 300 | 46.0 | 83.4 | 14.5 | 2.1 |
| 310 | 46.9 | 83.0 | 15.0 | 2.0 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the gas-phase hydrogenolysis of chlorofluorocarbons or of chlorofluorohydrocarbons in the presence of a palladium-based catalyst deposited on a support, comprising sulfur is incorporated into the catalyst.

2. Process according to claim 1, wherein the amount of sulfur per gram of palladium is between 0.75 and 750 mg, preferably between 2 and 100 mg and more particularly between 7.5 and 75 mg.

3. Process according to claim 1, wherein the palladium represents from 0.1 to 10% of the total weight of the catalyst.

4. Process according to claim 1 wherein in which the sulfur in incorporated into the catalyst using a precursor selected from sulfur chloride, sulfur dichloride, carbon disulphide, thiophene, hydrogen sulphide, methyl mercaptan and dimethyl sulphide.

5. Process according to claim 1 wherein the sulfur is incorporated into the catalyst by impregnation using a solution of a precursor which is normally liquid, and treatment under hydrogen at a temperature of between 150° and 400° C.

6. Process according to claim 5, wherein an ethanolic solution of carbon disulphide is used.

7. Process according to claim 1 wherein the sulfur is introduced onto the catalyst via the gaseous phase before and/or during hydrogenolysis reaction.

8. Process according to claim 7, wherein the precursor introduced in gaseous form is hydrogen sulphide, methyl mercaptan or carbon disulphide.

9. Process according to claim 1 comprising hydrogenolysis of chloropentafluoroethane to pentafluoroethane.

10. Process according to claim 1 comprising purification of a crude pentafluoroethane containing chloropentafluoroethane.

11. Process according to claim 2, wherein the amount of sulfur per gram of palladium is between 2 and 100 mg.

12. Process according to claim 2, wherein the amount of sulfur per gram of palladium is between 7.5 and 75 mg.

* * * * *